United States Patent
Trainer

(10) Patent No.: US 10,113,945 B2
(45) Date of Patent: Oct. 30, 2018

(54) METHOD AND APPARATUS FOR COMBINING MEASUREMENTS OF PARTICLE CHARACTERISTICS USING LIGHT SCATTERING AND OPTICAL IMAGING

(71) Applicant: Michael Trainer, Coopersburg, PA (US)

(72) Inventor: Michael Trainer, Coopersburg, PA (US)

(73) Assignee: MICROTRAC INC., Montgomeryville, PA (US)

( * ) Notice: Subject to any disclaimer, the term of this patent is extended or adjusted under 35 U.S.C. 154(b) by 0 days.

(21) Appl. No.: 15/899,259

(22) Filed: Feb. 19, 2018

(65) Prior Publication Data

US 2018/0188148 A1   Jul. 5, 2018

Related U.S. Application Data

(63) Continuation-in-part of application No. 15/590,628, filed on May 9, 2017, now Pat. No. 9,897,524.

(60) Provisional application No. 62/333,943, filed on May 10, 2016.

(51) Int. Cl.
*G01N 15/02*   (2006.01)

(52) U.S. Cl.
CPC ..... *G01N 15/0211* (2013.01); *G01N 15/0227* (2013.01)

(58) Field of Classification Search
CPC .............................. G01N 15/02; G01N 15/14
USPC .......................................................... 356/336
See application file for complete search history.

(56) References Cited

U.S. PATENT DOCUMENTS

| | | | | |
|---|---|---|---|---|
| 5,056,918 A * | 10/1991 | Bott | ................... | G01N 15/0211 356/336 |
| 5,918,272 A * | 6/1999 | Snyder | ................... | B03C 1/288 210/222 |
| 6,104,491 A * | 8/2000 | Trainer | ................... | G01N 15/02 356/246 |
| 8,705,040 B2 | 4/2014 | Trainer | | |
| 9,297,737 B2 | 3/2016 | Trainer | | |
| 2007/0019195 A1* | 1/2007 | Totoki | ................ | G01N 15/0211 356/336 |
| 2014/0368820 A1* | 12/2014 | Sugasawa | .......... | G01N 15/0211 356/336 |

* cited by examiner

*Primary Examiner* — Roy M Punnoose

(57) ABSTRACT

The present invention comprises methods and apparatus for measuring light scattering from particles and images of particles, and for combining size distributions from the measurements to produce a single size distribution over a larger size range.

6 Claims, 2 Drawing Sheets

METHOD AND APPARATUS FOR COMBINING MEASUREMENTS OF PARTICLE CHARACTERISTICS USING LIGHT SCATTERING AND OPTICAL IMAGING

CROSS-REFERENCE TO PRIOR APPLICATIONS

This is a continuation-in-part of U.S. patent application Ser. No. 15/590,628, filed May 9, 2017, which claims the priority of U.S. provisional application Ser. No. 62/333,943, filed May 10, 2016.

BACKGROUND OF INVENTION

This invention relates to systems and methods for analyzing particles using light scattering from particles and imaging of particles.

SUMMARY OF INVENTION

The present invention comprises methods and apparatus for measuring light scattering from particles and images of particles. A first particle size distribution is determined from light scattering measurements; and a second particle size distribution is determined from imaging measurements. The first and second particle size distributions are combined into a single particle size distribution which covers a broader particle size range.

DETAILED DESCRIPTION OF THE INVENTION

Figure 1:
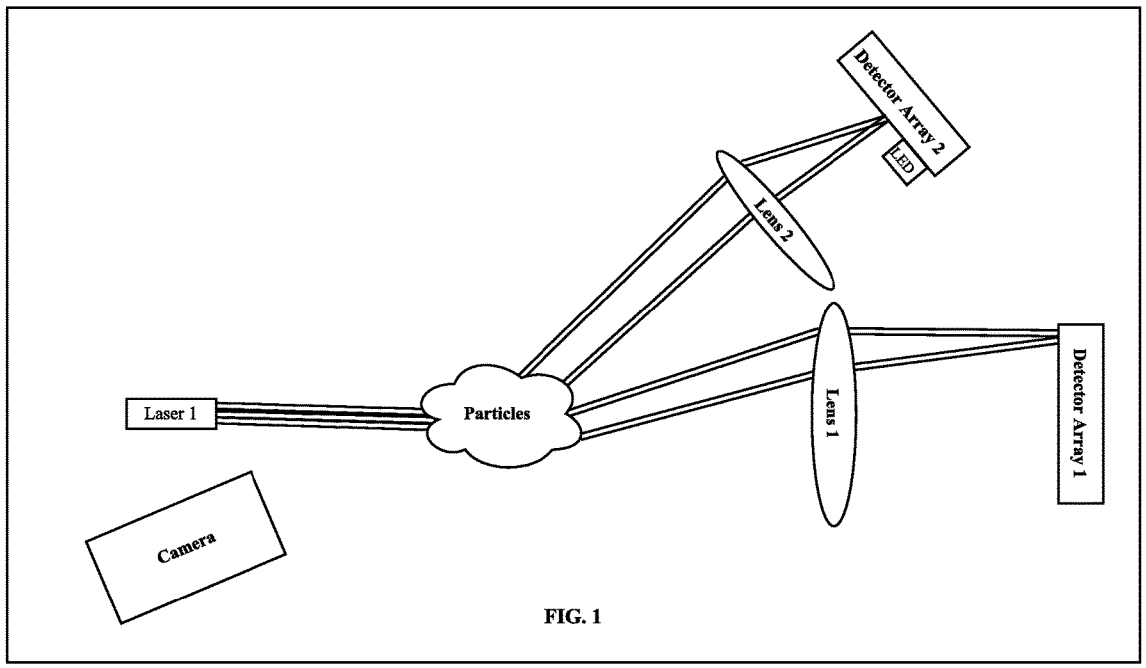
FIG. 1 describes an optical configuration for measurement of scattered light from particles.

The invention relates to the measurement of characteristics of small particles, wherein the characteristics include particle size distributions, including particle volume per particle diameter interval, particle area per particle diameter interval, and particle number per particle diameter interval. U.S. Pat. No. 5,416,580 describes an example of a static scattering method and apparatus for measuring scattered light. Diffraction or static scattering systems determine particle size distribution by analyzing the angular scattering distribution from an ensemble of particles. This angular scattering distribution can include scattered light flux per scattering angle interval or scattered light intensity vs. scattering angle. Analysis of scattering measurements can accurately determine the size of small particles down to diameter of 10 nanometers. Large particles scatter light at very low scattering angles, where background scatter from optics can interfere with accurate measurement of the angular scattering distribution. Therefore, scattering methods may show poor accuracy for large particle size measurement. Imaging methods provide an effective complimentary particle size measurement method to light scattering. Imaging methods measure larger particles with high accuracy. However, since the ultimate resolution of imaging is limited by diffraction of the imaging optical system, optical imaging cannot accurately measure very small particles. Therefore, the combination of optical imaging and light scattering methods and apparatus is effective for measuring accurate particle size over a large particle size range by utilizing each methodology to measure particles in the size range where that methodology provides optimum performance. Angular light scattering measurements are utilized to measure particles in the small size portion of the full size range and optical imaging measures the size of particles in the large size portion of the full size range. The size ranges of both methods are designed to have significant overlap in size to provide a common size region where the two size distributions are combined and scaled.

Each method of scattering or imaging can measure portions of the same generally homogeneous particle dispersion. Each method can also measure separate particle dispersions which have generally the same particle characteristics. This matching of particle dispersions for each method can be insured by designing an optical system such that each method measures particles which flow through the same sample cell, which includes windows to allow optical access to particles passing through the cell. This optical access can include both access for illumination of a particle dispersion and reception of light from particles. Therefore, the scattering measurements and imaging measurements will produce particle size distributions, which are representative of the same particle dispersion. This common representation can also be insured by measuring many different portions of the same dispersion and averaging those results for each method. In some cases, the imaging optical system and scatter measuring system each have a separate light source, which can be illuminated over specific time periods to avoid interactions between the two systems. In this way, the scattering detectors do not receive light scattered from the imaging light beam and the particle images of the imaging system do not contain imaging artifacts created by particle illumination from the scattering light source. In particular, the scattering light source is usually a laser source, which produces high intensity for scattering measurements, but which would provide images with coherent light artifacts. The imaging system can utilize a generally incoherent source to avoid these coherent light artifacts. In cases where the angle between the two light source beams is large, the detected particle scattered light from the scattering light source will be negligible in the imaging detector as compared to the detected particle imaging light from the imaging light source. In these cases, the scattering light source can remain on during the imaging process. The application of the claimed invention is not limited to the apparatus described above. This invention can be applied to combination of size distributions from any static scattering and imaging systems, including the case where these two systems are separate systems.

Figure 2:
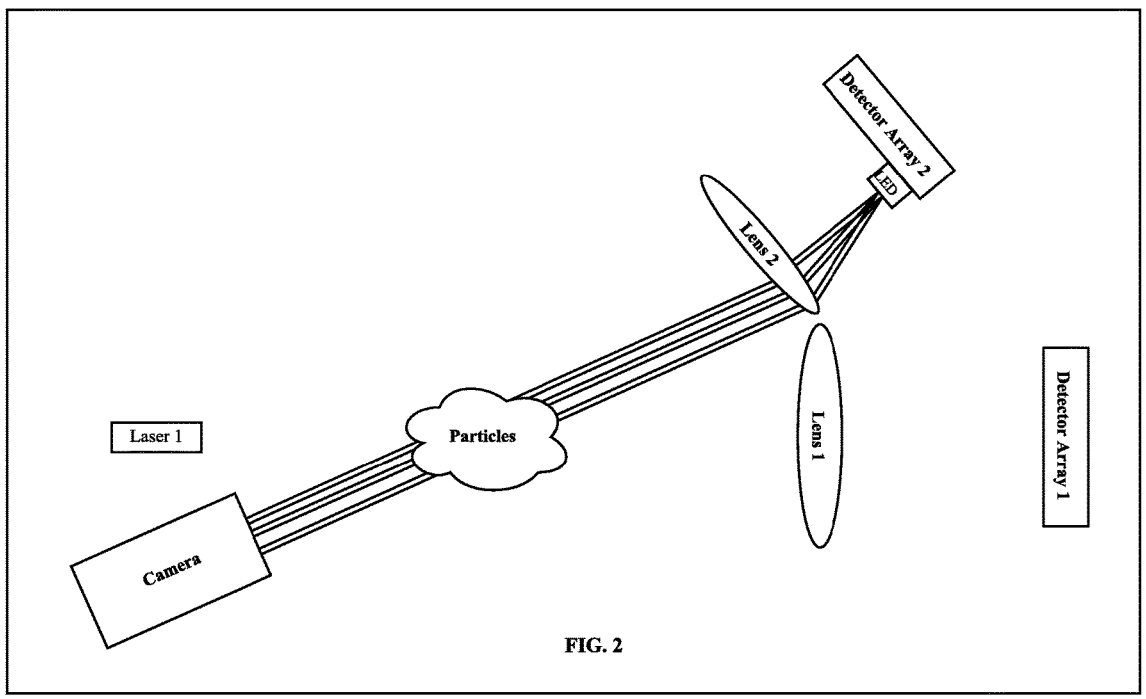
FIG. 2 describes an optical configuration for measurement of images from particles.
Figure 3:
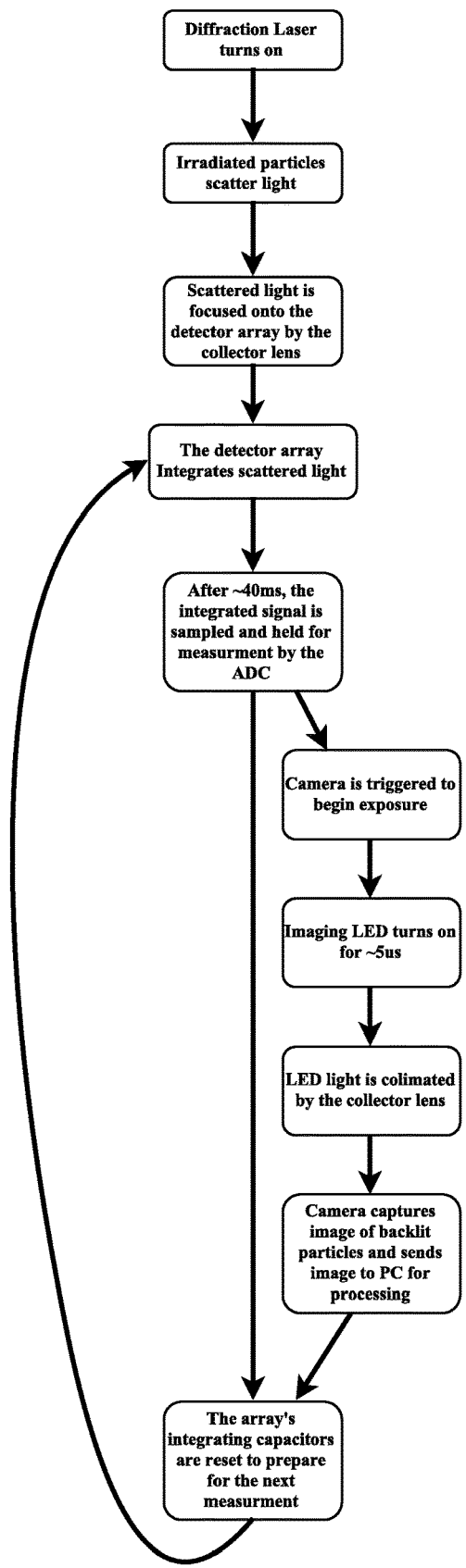
FIG. 3 describes the process flowchart of collecting scattering and imaging measurements.

FIGS. 1, 2, and 3 show an example of a system which produces the information utilized by the claimed invention. However, application of the claimed invention is not limited to this example. During a diffraction or static scattering measurement, a light source, such as a laser, irradiates particles flowing through a sample cell or sample region, as shown in FIG. 1 or as described in U.S. Pat. No. 5,416,580, for example. Light scattered from these particles is focused onto a detector array by a lens. Each detector element measures scattered light over a different range of scattering angles. After an integration period, the measured values, of the detector array, are temporarily stored by the sample and hold capacitors. While these values are being multiplexed and read by the analog to digital convertor, the arrays are reset and their integrating capacitors are drained to prepare for the next diffraction measurement. The digital values can be stored in a storage device, such as RAM memory. The array reset occurs during a short period, such as 5 milliseconds. During this reset period, a camera performs an exposure of at least one image of a particle dispersion, using a source such as a LED (light emitting diode), which flashes for a short period, as shown in FIG. 2, for example. The resulting digital imaging data can be stored in a storage device, such as RAM memory. Multiple performances of scatter light integration/digital storage and image detection/digital storage can be repeated until sufficient particles have been measured. In cases where space is limited, the light from the LED can be collimated by the same lens that focused the scattered light from the diffraction measurement, as shown by lens 2 in FIG. 2 for example. This light illuminates the sample particles from behind, allowing the camera to capture an image of the particle profiles. Because the LED only flashes while the arrays are being reset, the diffraction data is not impacted by the LED light. This allows for sequential diffraction and imaging measurements to be taken using a single sample cell. This process is also described in the process flowchart of FIG. 3.

A separate particle size distribution is created from each of these measurements. The light scattering distribution of scattered light flux vs. scattering angle range is measured from groups of particles. This scattering distribution is then inverted by an algorithm to produce a first uncorrected particle size distribution, such as particle volume per particle diameter range over a set of particle diameter ranges, for example. The particle volume distribution is the set of values of total particle volume in each interval of particle size or diameter. The group of size or diameter intervals span the size range of the scatter measuring method. The particle diameter is an effective particle diameter when non-spherical particles are measured. This effective particle diameter can be based upon the diameter of a sphere of equivalent volume or area to the non-spherical particle, for example. The inversion algorithm can utilize any angular scattering inversion algorithms, including deconvolution, to determine a particle size distribution from the angular scattering distribution.

The imaging system produces images of each particle which is in the field of the imaging optical system during exposure from a light source, which includes sources such as a LED. The pulse length of the LED is short to avoid elongated particle images due to particle motion during the LED illumination period. The dimensions of each particle image are measured and these dimensions are utilized to calculate an effective particle diameter for each particle. The effective particle diameter of each counted particle can also be determined from the area of each particle image, for example. The effective diameters for the particles are sorted into different particle size intervals or ranges to produce a second uncorrected distribution of particle number or count vs. particle diameter or size. The particle count or number distribution is the number of particles in each interval of particle size or diameter. The group of size or diameter intervals span the size range of the image measuring method. Each of the two uncorrected distributions will usually result from averaging of many measurement cycles of scatter light integration/digital storage and image detection/digital storage to accumulate sufficient data from a representative sample of the particle dispersion and to utilize averaging to improve measurement accuracy. This method and apparatus, for creating the first and second uncorrected distributions, is an example of a process and apparatus which creates information to be used by the claimed invention. Application of the claimed invention is not limited to this example. The claimed invention can utilize particle size distributions derived from any angular scattering system and any imaging system, utilizing any scattering inversion algorithm and any particle image sizing and counting algorithm.

Both of the first and second uncorrected distributions are converted to the same size distribution parameter, such as particle number per particle size interval, particle volume per particle size interval, or particle area per particle size interval to produce two corresponding distributions, with the same parameter and same size intervals. Typically the second particle size distribution from the imaging data is particle number per particle size interval, Nu2(di), at the ith value of effective particle diameter di. The distribution from scattering measurements could be particle volume per particle size interval, Vu1(di), at the ith value of equivalent particle diameter di, for example. The value di is the equivalent or effective particle diameter at the center of the ith particle size interval for both Nu2 and Vu1. Nu2 could be converted to a volume distribution, Vu2, by using the following equation to provide two corresponding distributions, with the same parameter of volume per particle size interval.

$$Vu2(di)=Nu2(di)*pi*(di\char`\^3)/6$$

Where pi is the known constant of approximately 3.1416, * is the multiply operator, and ^ is the power operator.

The imaging optical system and scattering measurement system are designed to have an overlapping size range, where the first distribution and second distribution overlap to create a common size region. Then the ratio of a sum of data points within a common size region between the two distributions is used to change the scale of one of the distributions to bring both distributions onto an equal amplitude scale, using the following procedure wherein Vu1 and Vu2 are uncorrected first and second particle size distributions, respectively, after conversion to the same type of parameter vs. particle size on the same particle size intervals.

$$V1(di)=Vu1(di)$$

$$V2(di)=k*Vu2(di)$$

$$k=\text{sum}(Vu1(a{:}b))/\text{sum}(Vu2(a{:}b))$$

Where di is particle diameter at the center of the ith particle size interval and V is the particle parameter per particle diameter interval. For the case where the distribution parameter is particle volume, V is the particle volume per particle size interval.

And k=sum(Vu1(a:b))/sum(Vu2(a:b)) where the size index range a:b defines a range in the common size region and sum(X(a:b)) is the summation of values of X(di) over the range i=a to i=b. In some cases, where both distributions, Vu1 and Vu2, cover the total size range of the particles, both distributions can be normalized to total number or total volume of particles without requiring scaling or using k=1.

The above process creates first distribution, V1, and second distribution, V2, from said first and second uncorrected distributions, respectively. After this scaling process, the two distributions, V1 and V2, are combined over a predetermined size overlap region, where both methods provide acceptable particle size accuracy over the same particle size region. Within this overlap region the two distributions are combined by the following equation:

first distribution (set of values) from scattering measurements: V1(di)
second distribution (set of values) from imaging measurements: V2(di)
Da=particle diameter at start of the overlap size region
Db=particle diameter at end of the overlap size region
Then the final combined distribution V(di) is given by:

$$V(di<Da)=V1(di<Da)$$

$$V(di>Db)=V2(di>Db)$$

$$V(Da<=di<=Db)=(1-Fi)*V1(di)+Fi*V2(di)$$

where Fi is a generally monotonic function of i such as a linear function for example:
Fi=(i−i1)/n where i=i1, i1+1, i1+2, . . . , i1+n and i1 is the size index corresponding to Da and i1+n is the size index corresponding to Db. In this example, the size overlap region contains n+1 size intervals.

The final combined distribution, V(di), can be converted to other types of distributions by using known methods. For example, if V(di) is particle volume per particle size interval, then particle number distribution, N(di), can be created by the following equation for example:

$$N(di)=6*V(di)/(pi*di^3)$$

This method for combining size distributions from static or angular scattering measurements and imaging measurements can be applied to measurements from any static scattering system and any imaging system which produce particle size distributions, including separate scattering and imaging systems.

What is claimed is:

1. An apparatus which determines a particle size distribution from scattering measurements of particles and imaging of particles comprising:
   a) at least one light source which illuminates particles,
   b) at least one scatter detector which detects light scattered from particles over a range of scattering angles,
   c) a plurality of imaging detectors which detect an image of each of a plurality of particles,
   d) means which determines a first particle size distribution from said detection of scattered light from particles,
   e) means which determines a second particle size distribution from said detection of images of particles,
   f) combining means which combines said first particle size distribution and said second particle size distribution to create a third particle size distribution with larger size range, wherein said third particle size distribution comprises three size regions which comprise a small size region, a size overlap region, and a large size region, wherein said third particle size distribution, in said small size region, is derived from a portion of said first particle size distribution, wherein said third particle size distribution, in said large size region, is derived from a portion of said second particle size distribution, and wherein said third particle size distribution, in said size overlap region, is derived from said first particle size distribution and said second particle size distribution, comprising the following means,
   g) means which places said first particle size distribution and said second particle size distribution onto the same scale and/or onto the same size distribution parameter, and
   h) means which combines said first particle size distribution and said second particle size distribution in said size overlap region to create said third particle size distribution in said size overlap region by utilizing a generally monotonic function of particle size.

2. The apparatus of claim 1, wherein said at least one scatter detector comprises a plurality of detectors to measure scattered light over a plurality of ranges of scattering angle.

3. The method of claim 1 wherein said generally monotonic function comprises a linear function.

4. A method which determines a particle size distribution from scattering measurements of particles and imaging of particles comprising:
   a) illuminating particles,
   b) detecting light scattered from particles over at least one range of scattering angle,
   c) detecting an image of each of a plurality of particles,
   d) determining a first particle size distribution from said detection of scattered light from particles,
   e) determining a second particle size distribution from said detection of particle images,
   f) combining said second particle size distribution and said first particle size distribution to create a third particle size distribution with larger size range, wherein said third particle size distribution comprises three size regions which comprise a small size region, a size overlap region, and a large size region, wherein said third particle size distribution, in said small size region, is derived from a portion of said first particle size distribution, wherein said third particle size distribution, in said large size region, is derived from a portion of said second particle size distribution, and wherein said third particle size distribution, in said size overlap region, is derived from said first particle size distribution and said second particle size distribution, comprising the following steps,
   g) placing said first particle size distribution and said second particle size distribution onto the same scale and/or onto the same size distribution parameter, and
   h) combining said first particle size distribution and said second particle size distribution in said size overlap region to create said third particle size distribution in said size overlap region by utilizing a generally monotonic function of particle size.

5. The method of claim 4 wherein said scattered light detecting utilizes a plurality of detectors to measure scattered light over a plurality of ranges of scattering angle.

6. The method of claim 4 wherein said generally monotonic function comprises a linear function.

* * * * *